US009119855B2

(12) United States Patent
Ford

(10) Patent No.: US 9,119,855 B2
(45) Date of Patent: *Sep. 1, 2015

(54) COMPOSITIONS AND METHODS FOR TREATMENT OF THE SIDE-EFFECTS ASSOCIATED WITH ADMINISTRATION OF CANCER CHEMOTHERAPEUTIC AGENTS

(71) Applicant: Asymmetric Therapeutics, LLC, Unadilla, NY (US)

(72) Inventor: John P. Ford, Unadilla, NY (US)

(73) Assignee: Asymmetric Therapeutics, LLC, Unadilla, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/162,155

(22) Filed: Jan. 23, 2014

(65) Prior Publication Data

US 2014/0134239 A1 May 15, 2014

Related U.S. Application Data

(63) Continuation-in-part of application No. 13/446,328, filed on Apr. 13, 2012, now Pat. No. 8,653,090, which is a continuation-in-part of application No. 12/381,474, filed on Mar. 12, 2009, now abandoned.

(60) Provisional application No. 61/069,031, filed on Mar. 12, 2008.

(51) Int. Cl.
| | |
|---|---|
| *A61K 31/513* | (2006.01) |
| *A61K 31/519* | (2006.01) |
| *A61K 31/52* | (2006.01) |
| *A61K 31/7004* | (2006.01) |
| *A61K 9/127* | (2006.01) |
| *A61K 45/06* | (2006.01) |
| *A61K 9/00* | (2006.01) |

(52) U.S. Cl.
CPC .............. *A61K 31/513* (2013.01); *A61K 9/0004* (2013.01); *A61K 9/127* (2013.01); *A61K 31/52* (2013.01); *A61K 31/7004* (2013.01); *A61K 45/06* (2013.01)

(58) Field of Classification Search
None
See application file for complete search history.

(56) References Cited

U.S. PATENT DOCUMENTS

| 6,723,737 | B1 | 4/2004 | Rapaport | |
|---|---|---|---|---|
| 6,995,165 | B2 | 2/2006 | Ford | |
| 8,034,823 | B2 | 10/2011 | Karmali | |
| 8,653,090 | B2 * | 2/2014 | Ford | 514/263.4 |
| 2009/0131344 | A1 | 5/2009 | Karmali | |
| 2012/0244211 | A1 | 9/2012 | Ford | |

OTHER PUBLICATIONS

Bartlett, "Erythrocyte Metabolism", pp. 10-13 in Adenine and Red Cell Storage, The Human Red Cell in Vitro, Greenwald et al., ed., New York: Grune and Stratton, 1974.
Borgström et al., "Studies of Intestinal Digestion and Absorption in the Human", J. Clin. Invest., vol. 36, pp. 1521-1536, 1957.
Bührdel et al., "Adenine Therapy in Lesch-Nyhan Syndrome", Acta Paediatrica Hungarica, vol. 26, pp. 327-333, 1985.
"Care During Chemotherapy", available at http://web.archive.org/web/20080310230202/http://www.chemocare.com/whatis/types_of_chemotherapy.asp, 3 pages, Mar. 10, 2008.
Fox et al., "Allopurinol Modulation of Fluorouracil Toxicity", Cancer Chemotherapy and Pharmacology, vol. 5, pp. 151-155, 1981.
Hoff, "The tegafur-based dihydropyrimidine dehydrogenase inhibitory fluoropyrimidines, UFT/leucovorin (ORZWL) and S-1: a review of their clinical development and therapeutic potential", Investigational New Drugs, vol. 18, pp. 331-342, 2000.
Ichikawa et al., "Orotate Phosphoribosyltransferase Gene Polymorphism Predicts Toxicity in Patients Treated with Bolus 5-Fluorouracil Regimen", Clinical Cancer Research, vol. 12, pp. 3928-3933, 2006.
Levine et al., "Autophagy in the Pathogenesis of Disease", Cell, vol. 132, pp. 27-42, 2008.
Lian et al., "Trends and Developments in Liposome Drug Delivery Systems", Journal of Pharmaceutical Sciences, vol. 90, pp. 667-680, 2001.
Ma et al., "High Glucose Induces Autophagy in Podocytes", Experimental Cell Research, vol. 319, pp. 779-789, 2013.
Plunkett et al., "Gemcitabine: Metabolism, Mechanisms of Action and Self-potentiation", Seminars in Oncology, vol. 4, pp. 3-10, 1995, abstract only.
Robinson et al., "Effects of Orotic Acid Ingestion on Urinary and Blood Parameters in Humans", Nutrition Research, vol. 3, pp. 407-415, 1983.
Roesly et al., "The Decreased Expression of Beclin-1 Correlates with Progression to Esophageal Adenocarcinoma: The Role of Deoxycholic Acid", Am J. Physiol. Gastrointest. Liver Physiol., vol. 302, pp. G864-G872, 2012.
Salati et al., "Absorption and Metabolism of Adenine, Adenosine-5'-Monophosphate, Adenosine and Hypoxanthine by the Isolated Vascularly Perfused Rat Small Intestine", Journal of Nutrition, vol. 114, pp. 753-760, 1984.
Torchilin, "Recent Advances with Liposomes as Pharmaceutical Carriers", Nature Reviews: Drug Discovery, vol. 4, pp. 145-160, 2005.
Van Acker et al., "Complete Deficiency of Adenine Phosphoribosyltransferase", The New England Journal of Medicine, vol. 297, pp. 127-132, 1977.
Verma et al., "Osmotically Controlled Oral Drug Delivery", Drug Development and Industrial Pharmacy, vol. 26, pp. 695-708, 2000.
International Search Report and Written Opinion for PCT/US2013/036326, dated Jul. 29, 2013, 12 pages.

* cited by examiner

*Primary Examiner* — Robert M Kelly
(74) *Attorney, Agent, or Firm* — Brown & Michaels, PC

(57) ABSTRACT

A composition and method for the treatment of the side-effects associated with the administration of cancer chemotherapeutic agents involves the oral ingestion of a slow release capsule containing adenine. In some embodiments, the slow release capsule also contains orotate. The systemic administration of a proton pump inhibitor decreases systemic absorption of orotate, and the systemic administration of allopurinol decreases the formation of 2,8-dihydroxy adenine from adenine. In an alternative embodiment, cationic liposomes contain purine/pyrimidine precursors. The cationic liposomes bind to the cells lining the mucosa of the intestinal tract and then the contents of the cationic liposome are then taken up in the interior of the cells to prevent the metabolism of the cancer treatment drug 5-FU into a toxic species. A method for prevention of oral stomatitis and a method for treatment of dysplastic tissue are also disclosed.

13 Claims, 9 Drawing Sheets

A: 5FU (0.01 mM) O (0 mM) A (0 mM)
B: 5FU (0.01 mM) O (2.5 mM) A (0.62 mM)
C: 5FU (0.01 mM) O (2.5 mM) A (1.2 mM)
D: 5FU (0.01 mM) O (2.5 mM) A (2.5 mM)

A: 5FU (0.01 mM) O (0 mM) A (0 mM)
E: 5FU (0.01 mM) O (1.25 mM) A (0 mM)
F: 5FU (0.01 mM) O (1.25 mM) A (0.0125 mM)
G: 5FU (0.01 mM) O (1.25 mM) A (0.125 mM)
H: 5FU (0.01 mM) O (1.25 mM) A (1.25 mM)

A: 5FU (0.01 mM) O (0 mM) A (0 mM) I (0 mM)
D: 5FU (0.01 mM) O (2.5 mM) A (2.5 mM) I (0 mM)
I: 5FU (0.01 mM) O (2.5 mM) A (0 mM) I (2.5 mM)

A: 5FU (0.01 mM) O (0 mM) A (0 mM) U (0 mM)
D: 5FU (0.01 mM) O (2.5 mM) A (2.5 mM) U (0 mM)
J: 5FU (0.01 mM) O (2.5 mM) A (2.5 mM) U (1.25 mM)
K: 5FU (0.01 mM) O (2.5 mM) A (2.5 mM) U (2.5 mM)

COMPOSITIONS AND METHODS FOR TREATMENT OF THE SIDE-EFFECTS ASSOCIATED WITH ADMINISTRATION OF CANCER CHEMOTHERAPEUTIC AGENTS

REFERENCE TO RELATED APPLICATIONS

This is a continuation-in-part patent application of co-pending application Ser. No. 13/446,328, filed Apr. 13, 2012, entitled "COMPOSITIONS AND METHODS FOR TREATMENT OF THE SIDE-EFFECTS ASSOCIATED WITH ADMINISTRATION OF CANCER CHEMOTHERAPEUTIC AGENTS", which is a continuation-in-part patent application of application Ser. No. 12/381,474, filed Mar. 12, 2009, entitled "COMPOSITION AND METHOD FOR TREATMENT OF THE SIDE-EFFECTS ASSOCIATED WITH ADMINISTRATION OF CANCER CHEMOTHERAPEUTIC AGENTS", now abandoned, which claims one or more inventions which were disclosed in Provisional Application No. 61/069,031, filed Mar. 12, 2008, entitled "COMPOSITION AND METHOD FOR TREATMENT OF THE SIDE-EFFECTS ASSOCIATED WITH ADMINISTRATION OF CANCER CHEMOTHERAPEUTIC AGENTS". The benefit under 35 USC §119(e) of the United States provisional application is hereby claimed, and the aforementioned applications are hereby incorporated herein by reference.

BACKGROUND OF THE INVENTION

1. Field of the Invention

The invention pertains to the field of ameliorating the effect of drugs on the human body. More particularly, the invention pertains to a composition and a method for treatment of the side-effects associated with the administration of cancer chemotherapeutic agents, specifically 5-fluorouracil (5-FU).

2. Description of Related Art

Human beings who develop cancer are often treated with chemotherapeutic drugs. Cancer chemotherapeutic drugs, while effective at destroying a cancerous tumor, may also cause damage to normal tissues of the body. The normal tissues of the body most often affected by the side-effects of a cancer chemotherapeutic drug include the lining of the mouth, the lining of the intestine, and the hair. Symptoms associated with the deleterious effects of chemotherapeutic cancer drugs include hair loss, nausea, and vomiting. Occasionally, the side-effects associated with the administration of cancer chemotherapeutic drugs can be debilitating and result in interruptions of the cancer chemotherapeutic drug treatment regimen.

Various attempts have been made to lessen or to eliminate the symptoms associated with the administration of 5-fluorouracil (5-FU). One approach to mitigate the toxicity of 5-FU is to combine a 5-FU precursor drug with other agents such as oral oxonic acid and 5-chloro-2,4-dihydroxypyridine in the case of S-1. These agents have their own toxicities, including gastrointestinal (GI) toxicity (see, for example, Hoff, "The tegafur-based dihydropyrimidine dehydrogenase inhibitory fluoropyrimidines, UFT/leucovorin (ORZWL) and S-1: a review of their clinical development and therapeutic potential", *Investigational New Drugs*, Vol. 18, pp. 331-342, 2000). Other drugs, such as steroids, have been administered to patients to alleviate the suffering associated with the side-effects of cancer treatment using chemotherapy. The success associated with the use of these other drugs to alleviate suffering has not been successful, and as a consequence, the "treatment" is to lower the dose of 5-FU.

Another problem associated with these other drugs is that drugs such as steroids and other drugs used to alleviate the side-effects of cancer drugs may be toxic to other tissues. Such tissue toxicity produces additional unwanted side-effects.

A third problem associated with drugs administered to alleviate the side-effects of cancer therapy is that the drug used to alleviate the side-effects caused by the cancer drug may interfere with the activity of the cancer drug, resulting in diminished effectiveness for destroying the targeted cancerous tumor.

Accordingly, there remains a need in the art for a composition and method for the treatment of the side-effects associated with the administration of 5-FU and 5-FU precursor drugs, such as capecitabine.

SUMMARY OF THE INVENTION

A composition and method for the treatment of the side-effects associated with the administration of cancer chemotherapeutic agents involves the oral ingestion of a slow release capsule containing adenine. In some embodiments, the slow release capsule also contains orotate. The systemic administration of a proton pump inhibitor decreases systemic absorption of orotate, and the systemic administration of allopurinol decreases the formation of 2,8-dihydroxy adenine from adenine. In an alternative embodiment, cationic liposomes contain purine/pyrimidine precursors. The cationic liposomes bind to the cells lining the mucosa of the intestinal tract and then the contents of the cationic liposome are then taken up in the interior of the cells to prevent the metabolism of the cancer treatment drug 5-FU into a toxic species. A method for prevention of oral stomatitis and a method for treatment of dysplastic tissue are also disclosed.

DETAILED DESCRIPTION OF THE INVENTION

Figure 1:
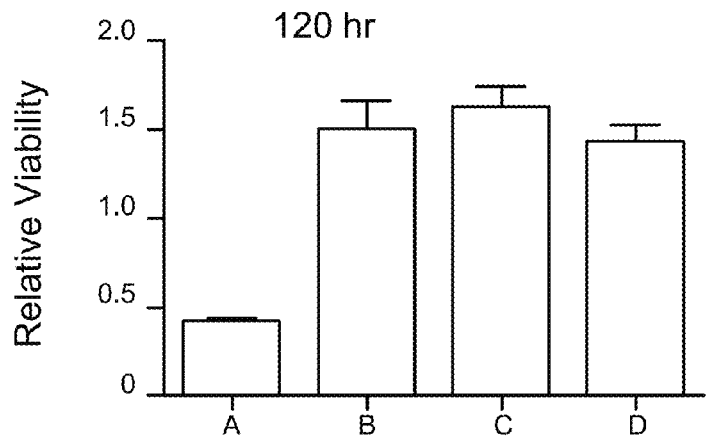
FIG. 1 shows the effect of different levels of adenine in combination with 2.5 mM orotate on the growth of human-derived colon (Caco-2) cells exposed to 5-FU in cell culture.

The approaches described herein to alleviate the toxicity of 5-FU to the GI tract and its associated suffering are to deliver the mitigating drug directly to the organ affected by the cancer treatment drug, which causes undesirable organ toxicity, in this case to the GI tract. This asymmetric delivery of toxicity prevention only to the tissue subject to the toxicity can allow a higher dose of anti-cancer medicine to be given to treat the cancer.

Compositions and methods for the treatment of the side-effects associated with administration of cancer chemotherapeutic agents are disclosed herein. A protective formulation is orally administered to the patient. The protective formulation includes at least one natural substrate of at least one enzyme that also metabolizes the cancer therapeutic agent. A substrate of an enzyme that metabolizes the cancer therapeutic agent, as used herein, may be any chemical that binds to the enzyme to a degree such that the rate of reaction between the enzyme and the cancer therapeutic agent decreases and the product of the substrate and the enzyme is a normal cell component.

In some embodiments, a protective formulation for 5-FU includes a mixture of adenine (A) and orotate (O) administered orally at concentrations in the range of 0.0074 mM to 2.5 mM of adenine and 0.0064 mM to 2.5 mM of orotate. In other embodiments, a protective formulation for 5-FU includes adenine (A), administered orally at a concentration in the range of 0.0074 mM to 2.5 mM, and no orotate (O). Experimental results in cell culture show 150% viability of control for growth in the presence of 0.625 mM adenine and 1.25 mM orotate with growth at 5 days despite the concomitant exposure to 0.01 mM of 5-FU. Exposure to adenine/orotate concentrations in the range of 0.001-0.0125 mM, resulted in no meaningful salvage of 5-FU toxicity administered at the physiologic dose of 0.01 mM. Importantly, both adenine and orotate are normal enzyme substrates and generate normal anabolites. There is no toxicity from their use together or without the concomitant exposure to 5-FU. Other purine and pyrimidine precursors, such as uracil and inosine do not attenuate, but actually exacerbate, the toxicity of 5-FU to human-derived colon (Caco-2) cells.

The salvage effect is quite specific. Interestingly, the metabolism of skin cells is different from GI cells, and uracil treatment actually reduces the toxicity of 5-FU to skin cells (squamous histology, see below).

Although improved results were obtained when the protective formulation was delivered by liposomes, it was also determined that administration of adenine and orotate in solution could protect cells from 5-FU toxicity.

Because the cells lining the mucosa of the intestinal tract are protected from the toxic effects of 5-FU by the protective formulation, the dosage of 5-FU or its active precursor may be increased so as to more effectively destroy the existing cancerous tumor. Moreover, since 5-FU is not being metabolized in the gastrointestinal tract, more 5-FU is available for destruction of the targeted cancerous tumor. Since the toxic side-effects associated with 5-FU metabolism have been ameliorated by the compositions and methods, normal homeostasis is maintained in the GI tract and patients receiving 5-FU for cancer therapy are more likely to adhere to the treatment regimen recommended by their physician. The combination of increased compliance and increased dosage of 5-FU afforded by the compositions and methods improves the outcome associated with 5-FU cancer treatment therapy.

In a preferred embodiment, adenine or adenine and orotate are delivered via an osmotically-controlled oral drug delivery system (see, for example, Verma, et al., "Osmotically Controlled Oral Drug Delivery", *Drug Development and Industrial Pharmacy*, Vol. 26, pp. 695-708, 2000). This system preferably delivers adenine or adenine and orotate to all the columnar cells throughout the GI tract.

In an alternative embodiment, the protective formulation includes cationic liposomes containing one or more of various purine/pyrimidine precursors that are administered orally to patients receiving 5-FU for cancer treatment. The cationic liposomes containing the purine/pyrimidine precursors bind to the cells lining the mucosa of the intestinal tract. After binding to the cells lining the mucosa of the intestinal tract, the substrate contents of the cationic liposomes are deposited into the interior of the cells lining the mucosa of the intestinal tract. The liposomally-transfected substrates prevent the metabolism of 5-FU into a toxic species, thereby protecting those cells into which the cationic liposome has been deposited from the toxicity associated with administration of 5-FU. The liposomally-transfected substrates protect the cells lining the mucosa of the intestinal tract from any toxicity associated with the administration of the substrate orotate.

The compositions and methods of treating the side-effects of cancer chemotherapeutic drug administration disclosed herein employ substrates of the enzymes which the human body uses to metabolize the cancer treatment drug.

In preferred embodiments, the substrates of the enzymes are incorporated into slow-release capsules. A particularly well-suited drug delivery format is an osmotically-controlled drug delivery system. A preferred use would be for the device to deliver the purine/pyrimidine precursor drug to the columnar cells throughout the GI tract, which extends from the base of the squamous cell-lined esophagus to the squamous cell-lined anus. The push-pull osmotic pump (PPOP) can provide the optimal zero-order release rate kinetics (see, for example, Verma et al.). The PPOP has been used to deliver drugs such as indomethacin and levodopa. Alternative delivery vehicles include devices such as pH-dependent, enzyme degradation-dependent, and matrix- or polymer-dependent devices.

In other embodiments, the substrates of the enzymes are incorporated into cationic liposomes. Such metabolic by-products and enzyme substrates are incorporated into the cationic liposomes to prevent the damage caused by the cancer drug. Oral administration of the slow-release capsules or cationic liposomes promotes incorporation of the enzyme substrates into the cells lining the mucosa of the intestinal tract to which the cancer drug is toxic. Thereby, the toxic effect of the cancer drug is minimized. These substrates of the enzymes used to metabolize the cancer treatment drug are nontoxic to normal tissues. By administering the substrates of the enzymes which metabolize the cancer chemotherapeutic drug orally, the substrates of the enzymes used to metabolize the cancer treatment drug are delivered only to the cells lining the mucosa of the intestinal tract and do not interfere with the activity of the cancer chemotherapeutic drug on the cancerous tumor to which the cancer chemotherapeutic drug is directed.

The compositions and methods are preferably specifically directed to a composition and method for alleviating the gastrointestinal side-effects of 5-fluorouracil (5-FU). The principle of applying locally an agent to reverse the toxicity of a chemotherapy agent may be applicable to alleviating the side-effects of other cancer chemotherapeutic drugs which cause GI toxicity. The cancer chemotherapeutic agent, 5-FU is one of the first cancer drugs identified and is commonly used in the treatment of cancers of the colon, breast, stomach, and other organs of the body. Among other side effects, the common side-effects of 5-FU administration are nausea and diarrhea because of the toxicity exerted by 5-FU on the cells lining the mucosa of the intestinal tract. The metabolic pathway for 5-FU is widely known.

The chemical 5-FU is inactive against cancerous tumors until it is metabolized by the body to the active species. Anabolism of 5-FU to its active species is accomplished by one of three alternate enzyme systems, which are as follows: 1) uridine phosphorylase (UP), 2) thymidine phosphorylase (TP), and 3) orotate phosphoribosyl transferase (OPT). There is evidence that metabolism of 5-FU by OPT results in the clinically-relevant cell toxicity to the gastrointestinal tract caused by 5-FU (see, for example, Ichikawa et al., "Orotate Phosphoribosyltransferase Gene Polymorphism Predicts Toxicity in Patients Treated with Bolus 5-Fluorouracil Regimen", *Clinical Cancer Research*, Vol. 12, pp. 3928-3933, 2006).

Enzymes such as UP, TP, and OPT can be blocked from acting on the primary substrate (e.g. 5-FU) by saturating the active site of the enzyme with a non-competitive substrate. Saturation of the active site of an enzyme with such a substrate decreases the availability of the enzyme for accepting the alternative substrate (e.g., 5-FU) at the active site of the enzyme, where it is metabolized by the enzyme. If a substance has decreased the active access to the enzyme, clearly this substrate is metabolized less by the enzyme.

Figure 2:
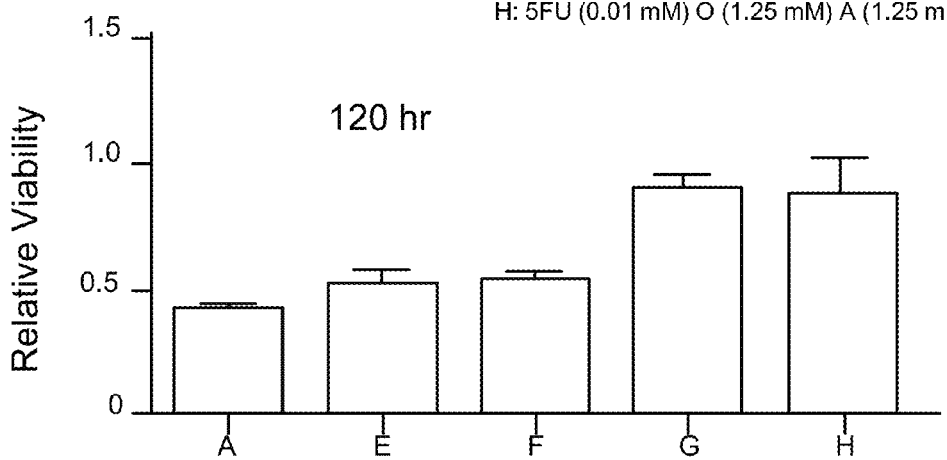
FIG. 2 shows the effect of different levels of adenine in combination with 1.25 mM orotate on the growth of human-derived colon (Caco-2) cells exposed to 5-FU in cell culture.
Figure 3:
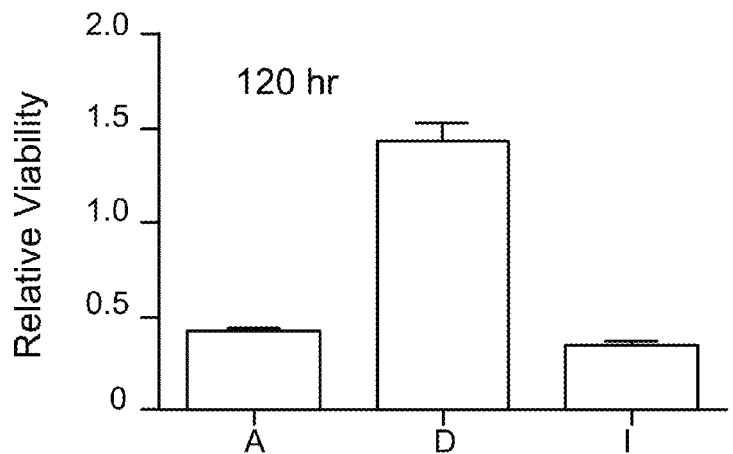
FIG. 3 shows the effect of adenine or inosine in combination with orotate on the growth of human-derived colon (Caco-2) cells exposed to 5-FU in cell culture.
Figure 4:
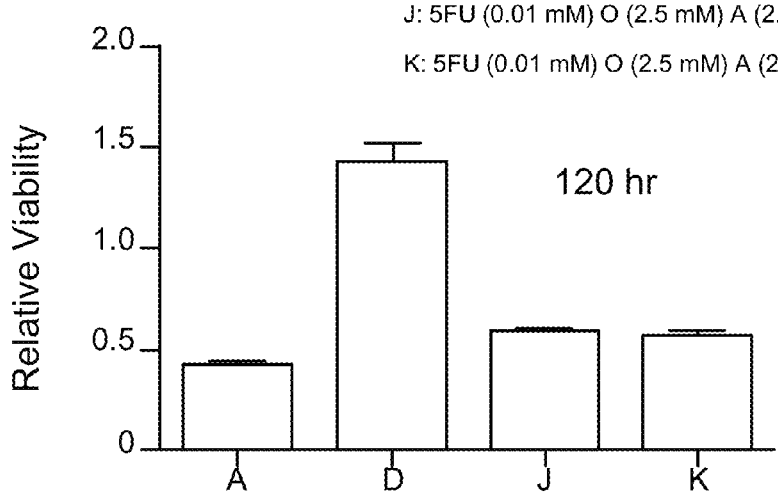
FIG. 4 shows the effect of different levels of uracil in combination with adenine and orotate on the growth of human-derived colon (Caco-2) cells exposed to 5-FU in cell culture.

The efficacy of certain compounds as protective agents when co-administered with 5-FU was tested in cell culture. In one set of experiments, the results of which are shown in FIG. 1, FIG. 2, FIG. 3, and FIG. 4, human-derived colon (Caco-2) cells, commonly used to assess colon cell toxicity, were exposed to the clinically-relevant dose of 0.01 mM 5-FU and different concentrations of orotate (O), adenine (A), uracil (U), and inosine (I) using standard tissue culture methods and incubated at 37° C. The relative viability of the cells was determined after 120 hours. With no orotate, adenine, uracil, or inosine, the relative viability at 120 hours cultured in the presence of 0.01 mM 5-FU was less than 50% that of control cultures incubated without 5-FU present (Result A). With exposure to 0.01 mM 5-FU, 2.5 mM orotate, and adenine in the range of 0.62 mM to 2.5 mM, the relative viability at 120 hours was about 150% as shown in FIG. 1 (Results B, C, and D), indicating that the orotate/adenine combination is able to protect the cells from the 5-FU toxicity. With exposure to 0.01 mM 5-FU, 1.25 mM orotate, and adenine in the range of 0.125 mM to 1.25 mM, the relative viability at 120 hours was about 100% as shown in FIG. 2 (Results G and H), indicating that the orotate/adenine combination is able to protect the cells from the 5-FU toxicity. With exposure to 0.01 mM 5-FU, 1.25 mM orotate, and 0.0125 mM or less of adenine, however, the relative viability at 120 hours was about the same as with no orotate or adenine, as shown in FIG. 2 (Results E and F). With exposure to 0.01 mM 5-FU and a combination of 2.5 mM orotate and 2.5 mM inosine the relative viability at 120 hours was less than 50% as shown in FIG. 3 (Result I), indicating that the orotate/inosine combination is not able to protect the cells from the 5-FU toxicity. With exposure to 0.01 mM 5-FU, 2.5 mM orotate, 2.5 mM adenine, and uracil in the range of 1.25 mM to 2.5 mM, the relative viability at 120 hours was slightly more than 50% as shown in FIG. 4 (Results J and K), indicating that the presence of uracil counteracts the effect of the orotate/adenine combination, and the cells are not protected from the 5-FU toxicity.

Figure 5:
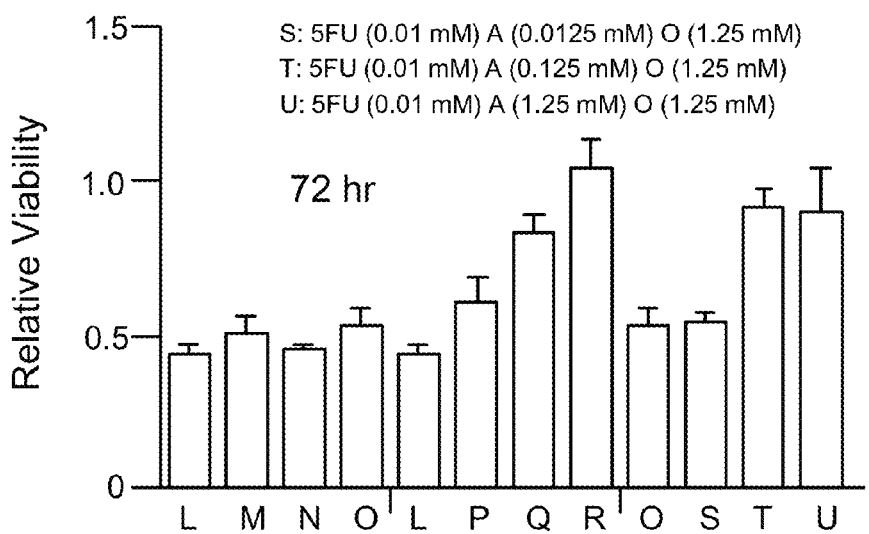
FIG. 5 shows the separate and combined effects of adenine and orotate on the growth of human-derived colon (Caco-2) cells exposed to 5-FU in cell culture.
Figure 6:
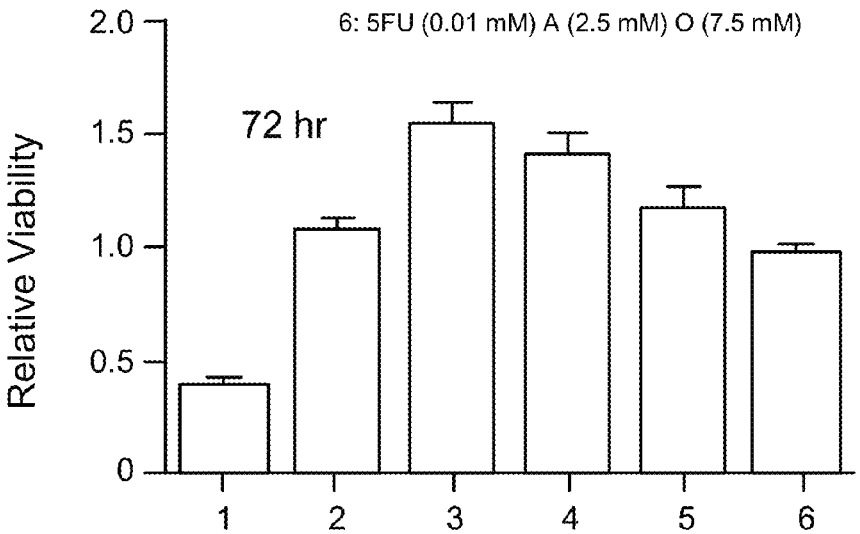
FIG. 6 shows the effect of orotate concentration on the combined effect of adenine and orotate on the growth of human-derived colon (Caco-2) cells exposed to 5-FU in cell culture.

FIG. 5 and FIG. 6 show the results of a more detailed examination of the cytoprotective effect of aqueous delivery of adenine and orotate both independently and in combination in Caco-2 cells on 5-FU toxicity at the clinically relevant exposure of 10 µM. To determine the dose-response relationships for adenine (A) and orotate (O) for protection of Caco-2 cells from 5-FU toxicity, cells were plated in 96-well plates and allowed to adhere overnight. Subsequently, cells were treated with adenine (A) and/or orotate (O), in concentration as shown in FIG. 5 and FIG. 6 (in mM). 5-FU was dissolved in water and added to media at 10 µM, the clinically-relevant dose. Media was changed every day with reapplication of 5-FU. After 72 hr, the cell viability was assessed and is expressed relative to a vehicle control (Caco-2, n=3).

Orotate alone at 0.0125 mM through 1.25 mM resulted in statistically insignificant cytoprotection against 10 µM 5-FU toxicity (FIG. 5, Results L, M, N, and O). In contrast, adenine alone at 0.0125 mM through 1.25 mM resulted in progressively greater cytoprotection against 10 µM 5-FU toxicity (FIG. 5, Results L, P, Q, and R). Quantitative protection with adenine alone appears to require a ~100× excess of the protective nucleobase.

Addition of orotate (1.25 mM) in combination with adenine did not initially attenuate 5-FU toxicity beyond the cytoprotection provided by adenine alone at 0.0125 mM through 1.25 mM (FIG. 5, comparing Results P and S, Results Q and T, and Results R and U). At higher concentrations of adenine (2.5 mM), the addition of orotate at 1.25 mM (FIG. 6, comparing Results 2 and 3) or 2.5 mM (FIG. 6, comparing Results 2 and 4) may provide enhanced protection against 5-FU toxicity in Caco-2 cells, with exposure to still higher concentrations of orotate resulting in progressively greater abrogation of salvage from 5-FU toxicity (FIG. 6, comparing Results 5 and 6 to Result 2).

In contrast to the nucleobase adenine (2.5 mM) in combination with orotate (2.5 mM), the nucleoside inosine (2.5 mM) in combination with orotate (2.5 mM) does not prevent 5-FU toxicity (data not shown), and a reversal of the cytoprotection provided by adenine (2.5 mM) in combination with orotate (2.5 mM) by the further addition of uracil (1.25 and 2.5 mM) was seen in the presence of 10 µM 5-FU (data not shown).

Figure 7:
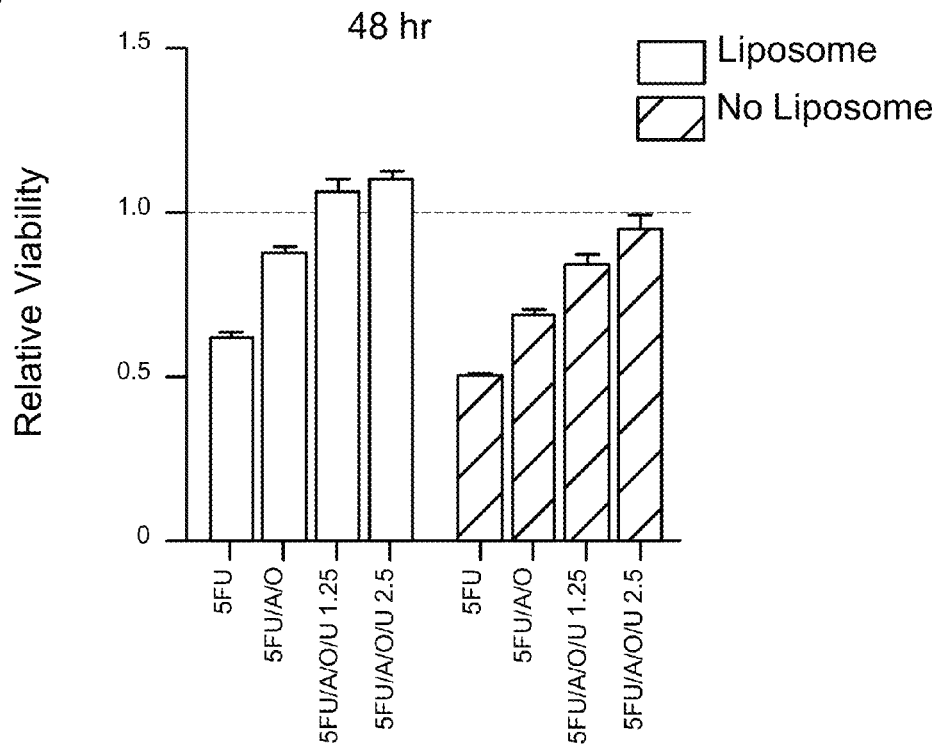
FIG. 7 shows the effect of adenine, orotate, and uracil on the growth of primary human skin cells exposed to 5-FU in cell culture after 48 hours.
Figure 8:
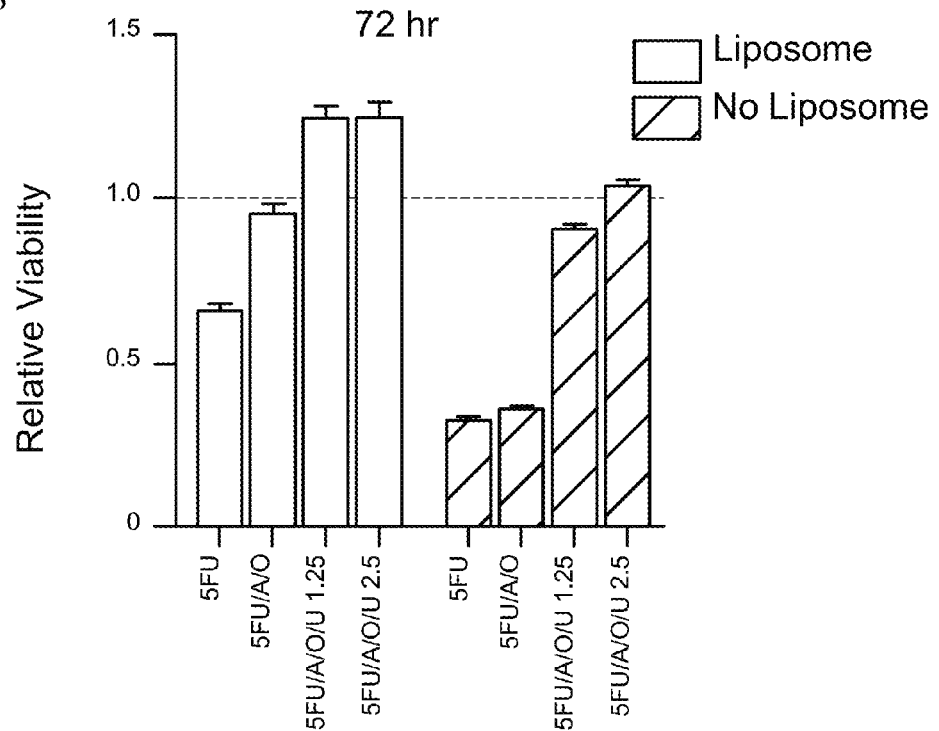
FIG. 8 shows the effect of adenine, orotate, and uracil on the growth of primary human skin cells exposed to 5-FU in cell culture after 72 hours.

FIG. 7 and FIG. 8 show the effect of different combinations of adenine (A), orotate (O), and uracil (U), either in liposomes or without liposomes, in mediating the toxicity to growth of 5-FU for human gingival cells in cell culture after incubation at 37° C. The concentration of 5-FU was also 0.01 mM in these trials. The concentration of adenine and orotate, when present, was 2.5 mM. The relative viability of the cells was determined after 48 hours (FIG. 7) or 72 hours (FIG. 8). In contrast to the human-derived colon (Caco-2) cell results, the inclusion of uracil with adenine and orotate actually increases the protection of the human skin cells against 5-FU toxicity, as shown in FIG. 7 and FIG. 8 (Results "5-FU/A/O/U 1.25" and "5-FU/A/O/U 2.5"). Although the adenine/orotate/uracil trials with liposomes produced greater relative cell viabilities than the adenine/orotate/uracil trials without liposomes, it should be noted that the 5-FU control trials with liposomes also produced greater relative cell viabilities than the equivalent trials without liposomes. It appears that liposomes may decrease the efficacy of 5-FU in vitro with unclear implications for the effect of oral liposomes on 5-FU toxicity in vivo.

Orotate is the natural substrate of the enzyme OPT. The activity of the enzyme OPT on 5-FU is decreased by the presence of an excess by saturating the active sites on the enzyme OPT by the natural substrate orotate. The production of toxic metabolite of 5-FU is reduced by the metabolism of 5-FU by the enzyme OPT because the active site of the enzyme OPT is filled with the competing substrate orotate. The competing substrate orotate inhibits 5-FU from entering the active site of the enzyme OPT where it can be further metabolized to the toxic product. Orotate, in comparison to 5-FU, is an acid with a much lower pK and therefore is a much better substrate for OPT.

The competing substrate orotate does not readily enter or exit the cell membrane of the cells lining the mucosa of the intestinal tract, because the substrate orotate has an acidic pK and an overall negative charge, as do the cell membranes of the cells lining the mucosa of the intestinal tract. At an acidic pH condition, the orotate is not charged and is better absorbed into the systemic circulation (see, for example, Robinson et al., "Effects of Orotic Acid Ingestion on Urinary and Blood Parameters in Humans", *Nutrition Research*, Vol. 3, pp. 407-415, 1983).

As mentioned above, 5-FU is also, alternatively, metabolized to its toxic form by the two enzymes UP and TP. Uracil can compete for anabolism with 5-FU via TP and UP. In conditions of excess uracil, the active site on the UP and TP enzymes are filled with uracil thereby decreasing the rate of metabolism of 5-FU by enzymes UP and TP to the toxic form. As noted in FIG. 3, the gland cells (columnar cells) that line the GI tract rely little on the salvage pathways of UP and TP. The result is that the use of uracil increases the toxicity of 5-FU. The likely explanation is that uracil competes well with 5-FU for UP and TP but is not active at all as a substitute for OPT because of its even higher pK than 5-FU (pK of uracil of 9.45>>pK of 5-FU of 7.8).

In contrast, skin cells (squamous), as shown in FIG. 7 and FIG. 8, have the reverse metabolic pathway. That is, TP/UP, in preference to OPT, are formed as squamous cells salvage pyrimidines to grow, as shown in FIG. 7 and FIG. 8. Thus, orotate does not impact skin (squamous) cell response to 5-FU exposure.

This result is intuitively consistent with how squamous cells grow, in layers, with the oldest at the top. As the top (superficial) layer of cells die, their contents are salvaged by the younger cell layer underneath.

Columnar cells absorb nutrition from the GI tract and make de novo pyrimidines. A layered structure would make no sense for nutrient-absorbing columnar cells as would using a strategy of nutrient salvage-dependent growth.

The competing substrate dietary orotate is nontoxic and requires facilitated transport to exit the cell because of its charge at neutral pH. At low pH, as in the stomach, the orotate is not ionized and is absorbed at a higher rate (see, for example, Robinson et al.). Then the orotate/adenine mixture may be given together with a proton pump inhibitor (PPI), which may include, but is not limited to, omeprazole, lansoprazole, dexlansoprazole, esomeprazole, pantoprazole, rabeprazole, and ilaprazole, to retain orotate within the GI tract and reduce systemic exposure to orotate. Proton pump inhibitors have the following chemical structure:

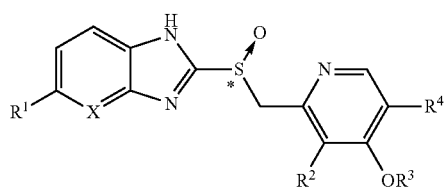

(1)

It has been observed that cellular exposure to enough orotate, such that the orotate permeates the cell membrane, depletes phosphoribosyl pyrophosphate (PRPP), which is depleted by the enzymatic action of OPT. As de novo purine synthesis also requires consumption of PRPP, the depletion of PRPP by unopposed OPT activity can cause cell death by depleting cellular PRPP pools. This results in decreased purine synthesis and can cause "purine less death". This cellular growth imbalance and tumor formation may be neutralized by the addition of adenine. Adenine is anabolized by phosphoribosyltransferase (APRT) to adenosine monophosphate that is converted by adenosine monophosphate deaminase (AMD) to inosine monophosphate (IMP), a GMP precursor. Thus, "purine less death" is avoided.

The present methods and compositions may have much wider application to treat GI disorders. As can be seen in FIGS. 1, 3, and 4, the exposure of human-derived colon (Caco-2) cells grew better in the presence of a combination of adenine, orotate, and 5-FU than controls without 5-FU. Adenine has in the past been noted to prolong the shelf life of stored blood (see, for example, Bartlett, "Erythrocyte Metabolism", pp. 10-13 in *Adenine and Red Cell Storage, The Human Red Cell in Vitro*, Greenwald et al., ed., New York: Grune and Stratton, 1974).

Adenine, unlike orotate, is uncharged and well-absorbed systemically. Adenine can, however, then be oxidized to 2,8-dihydroxy adenine. 2,8-dihydroxy adenine is poorly soluble and can cause renal stones (see, for example, Van Acker et al., "Complete Deficiency of Adenine Phosphoribosyltransferase", *The New England Journal of Medicine*, Vol. 297, pp. 127-132, 1977). The systemic exposure to adenine must be kept to a minimum.

Adenine also can reverse the systemic toxicity of 5-FU at high doses, which is another reason adenine exposure must be kept to a minimum. FIG. 2 shows that 1.25 mM orotate and 0.125 mM adenine can protect cells from the toxicity of 0.01 mM 5-FU exposure to cell growth, whereas decreasing the concentration of adenine to 0.0125 mM with orotate exposure at 1.25 mM offers no protection from the toxicity of 0.01 mM 5-FU exposure to cell growth.

It has been estimated that systemic exposure (i.e. by intravenous administration) to adenine in a single dose at 20 mg/kg to a human is safe (see, for example, Bartlett). For a 70 kg man, the adenine dosage would be 1.4 g. In the present instance, a 0.125-mM solution of adenine in a liter volume of GI fluid would be a 15 mg total body adenine exposure. Experiments have shown extraction efficiencies in the range of 75% to 85% of adenine introduced in the small intestine in rats (see, for example, Salati et al., "Absorption and Metabolism of Adenine, Adenosine-5'-Monophosphate, Adenosine and Hypoxanthine by the Isolated Vascularly Perfused Rat Small Intestine", *Journal of Nutrition*, Vol. 114, pp. 753-760, 1984). The systemic circulation volume for humans is about 5 liters. Therefore, the systemic exposure to adenine would be well below 1% of 20 mg/kg, which would neither cause renal stones nor rescue 5-FU.

In a preferred embodiment, a slow or controlled release dosage of adenine or adenine and orotate is given orally. More preferably, the oral delivery is osmotically-controlled oral drug delivery. A proton pump inhibitor (PPI) is preferably also given concomitantly to cause secretion of neutral gastric juices to prevent orotate absorption in the stomach. Also, allopurinol is preferably administered to decrease conversion of adenine to 2,8-dihydroxy adenine (see, for example, Bührdel et al., "Adenine Therapy in Lesch-Nyhan Syndrome", *Acta Paediatrica Hungarica*, Vol. 26, pp. 327-333, 1985).

In an alternative embodiment, a method and composition promote accumulation of the substrate orotate in the cells lining the mucosa of the intestinal trace by incorporating the substrate orotate with certain substrates of the enzymes into cationic liposomes. Cationic liposomes carry a net positive charge. This net positive charge enables the cationic liposome to be taken up by the negatively charged outer membranes of the cells lining the mucosa of the intestinal tract. By incorporating the substrate orotate and other substrates of enzymes into cationic liposomes, the substrate orotate and the other substrates of enzymes can be delivered to the cells lining the mucosa of the intestinal tract and then be taken up by the individual cells of the intestinal tract. Once taken up by the individual cells of the intestinal tract, the competing substrate orotate can then reduce the activity of the enzyme OPT in metabolizing 5-FU to its toxic by-product by saturating the active site of the enzyme OPT. This saturation of the active site of the enzyme OPT decreases further metabolism of 5-FU by the enzyme OPT. The cells lining the mucosa of the intestinal tract are thus relatively protected from the toxic, active 5-FU metabolites. The purine/pyrimidine substrates included in the cationic liposome further decrease the metabolism of 5-FU. The cationic liposomes, because of their charge, minimally permeate the body and release the substrate orotate to alter 5-FU metabolism in the cancerous tumor.

Many cationic lipids have been developed and used in cationic liposome preparation. While the cationic lipids have many different chemical structures, cationic lipids are all composed of a cationic head group composed of primary, secondary, tertiary, or quaternary amines. The primary, secondary, tertiary, or quaternary amines are attached to a hydrophobic group via a linker.

When placed in an aqueous solution, the cationic lipids form liposomes in which the cationic head is on the outside surface of the liposome and the hydrophobic group is on the inside of the liposome. By use of this process a three dimensional bag or sack is formed. The three-dimensional bag or sack contains the substrate orotate and other substrates of enzymes within the interior of the cationic liposome. Since the cationic head of the lipid is located on the surface of the cationic liposome, the positive charge associated with the cationic lipid is located on the outside surface of the cationic liposome.

Some of the commercially available cationic lipids and their suppliers are listed below:
  Lipofect ACE (Life Technologies)
  Lipofection (Life Technologies)
  LipofectAmine (Life Technologies)
  CeliFectin (Life Technologies)
  DMRIE-C (Life Technologies)
  DDAB (Sigma)
  DC-Chol (Sigma)
  DOTAP (Boehringer Mannheim, Avanti Polar Lipids, Biontex)
  MRX-230 and MRX-220 (Avanti Polar Lipids)
  Transfectam (Promega)
  Transfast (Promega)
  Tfx 10, Tfx 20, and Tfx 50 (Promega)
  Prefection-CaPO$_4$ (Promega)
  Prefection-DEAE-Dextran (Promega)
  GeneSHUTTLE-40 (Quantum Biotechnologies)
  CLONfectin (Clontech)
  METAFECTENE (Biontex)
  INSECTOGENE (Biontex)
  Effectene (Qiagen)
  FuGENE 6 (Roche Molecular Biochemicals)
  GENESEAL (MTTI)

In preparing the cationic liposome, a cationic lipid or a combination of cationic lipids are dissolved in an organic solvent such as chloroform or methanol. The solvent is then removed by use of a vacuum or by blowing an inert gas over the solution followed by rehydration in an aqueous solution. The aqueous solution used for rehydration contains the substrate orotate and other substrates of enzymes which metabolize the cancer treatment drug. As the cationic liposome forms due to hydrophobicity of the cationic lipids, the aqueous solution containing the substrate orotate and other substrates of enzymes which metabolize the cancer treatment drug are trapped within the interior of the cationic liposome. The cationic liposomes containing the substrate orotate and other substrates of enzymes which metabolize the cancer treatment drug are then made to a uniform size by either sonication or membrane extrusion.

The cationic liposome is a targeted vector to gastro-intestinal mucosa and does not provide a systemic source of nucleotide precursors.

Those of ordinary skill in the art will understand that in some embodiments, liposomes are used to deliver a purine or pyrimidine substrate to the cells lining the mucosa of the intestinal tract without raising the systemic levels of the delivered material. The reason for not raising the systemic levels of the delivered material is that a substance such as the substrate orotate may salvage a tumor from the effects of the 5-FU chemotherapy. Liposomes have never been used to accomplish this function. Rather, liposomes are typically used to cause a substance to enter a cancerous tumor or to enter into an organ such as the liver. Herein, a substance like the substrate orotate is used only to get into the cells lining the mucosa of the intestinal tract. Such function then becomes an asymmetric drug delivery system and method wherein different amounts of a drug are delivered to different parts of the body.

Figure 9:
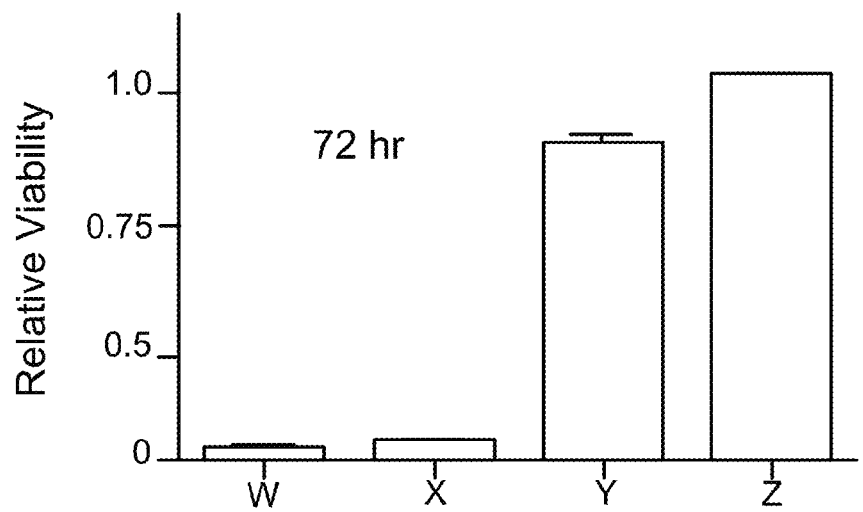
FIG. 9 shows the effect of uracil on the growth of primary human epithelial cells of the gingiva exposed to 5-FU in cell culture after 72 hours.
Figure 10:
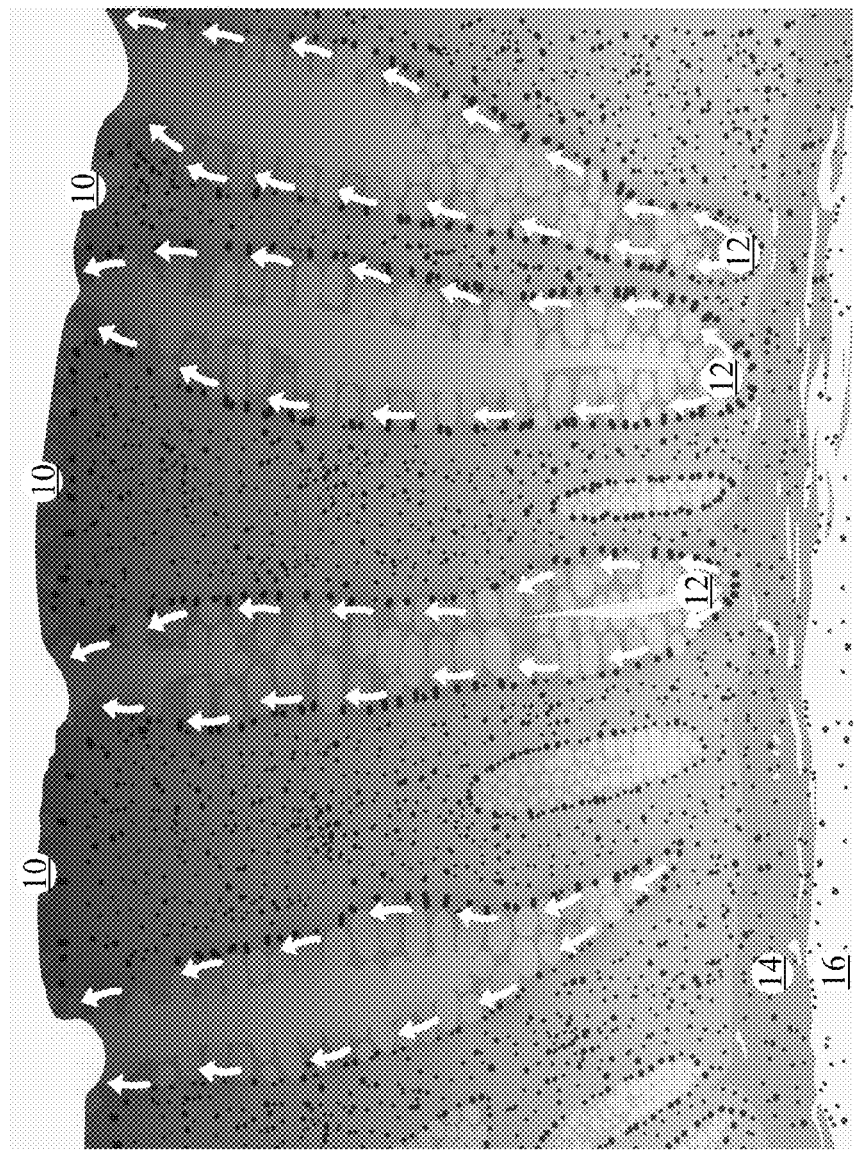
FIG. 10 shows a schematic micrograph of normal GI glandular mucosa.
Figure 11:
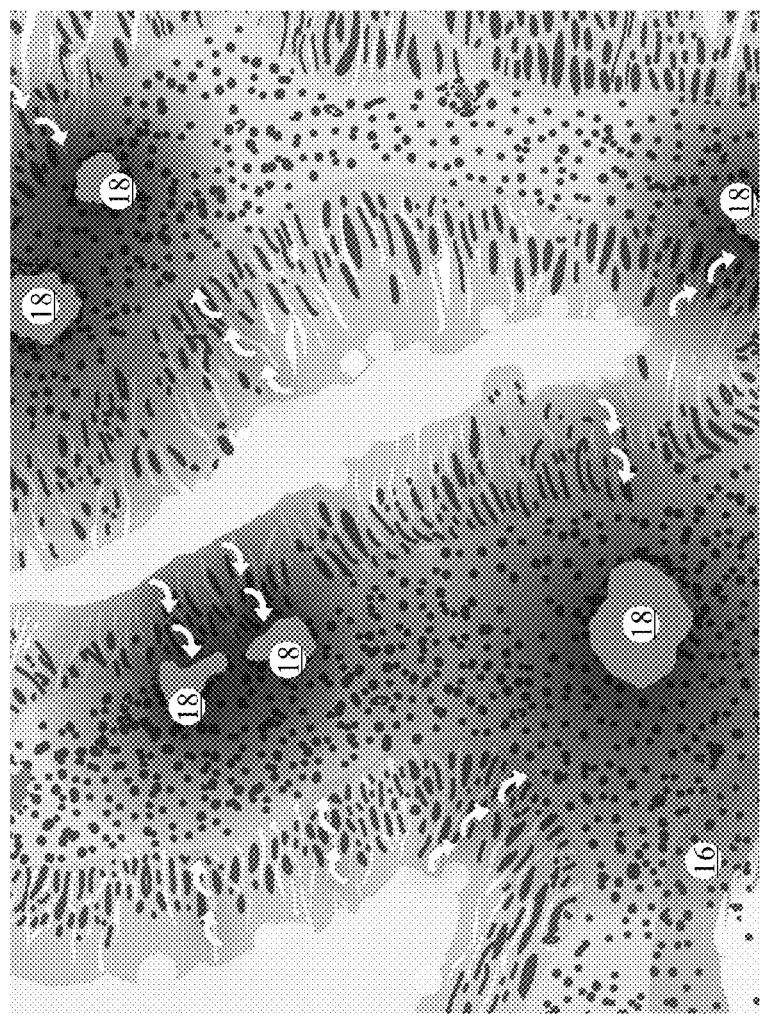
FIG. 11 shows a schematic micrograph of dysplastic GI glandular mucosa.
Figure 12:
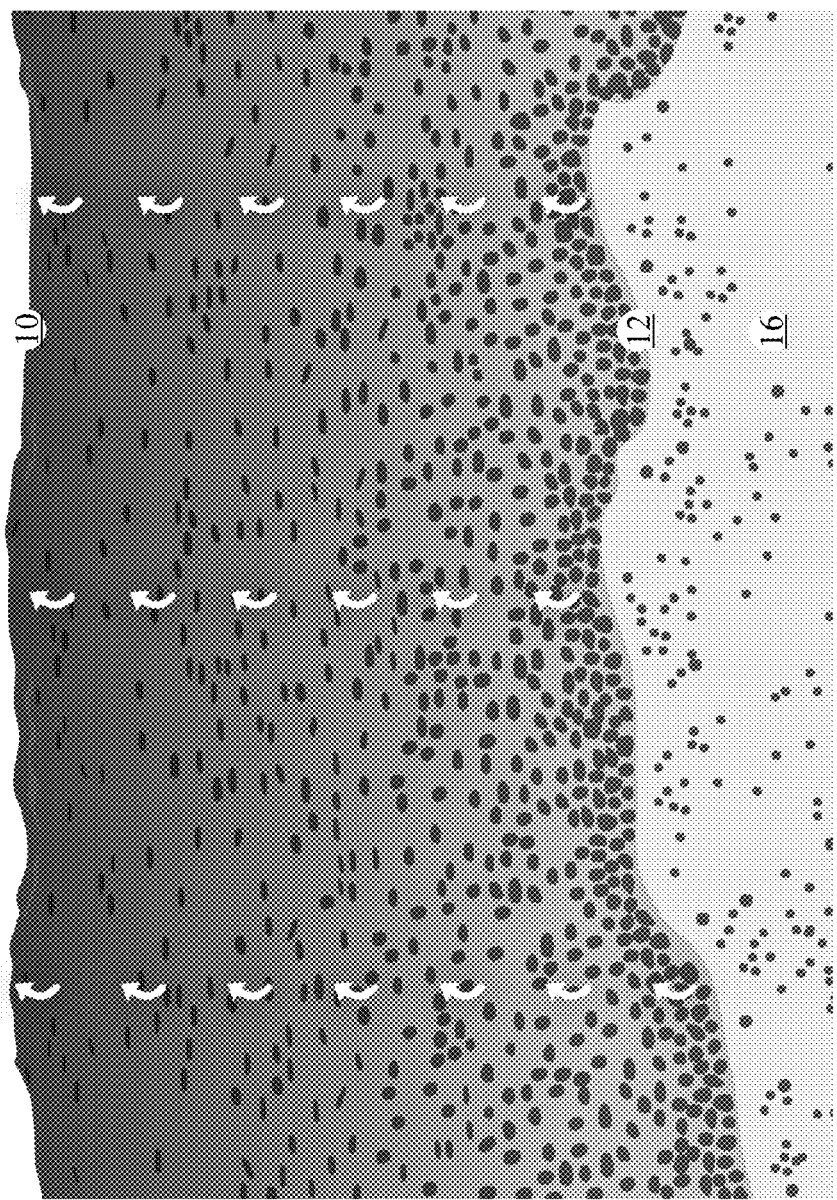
FIG. 12 shows a schematic micrograph of normal squamous mucosa.
Figure 13:
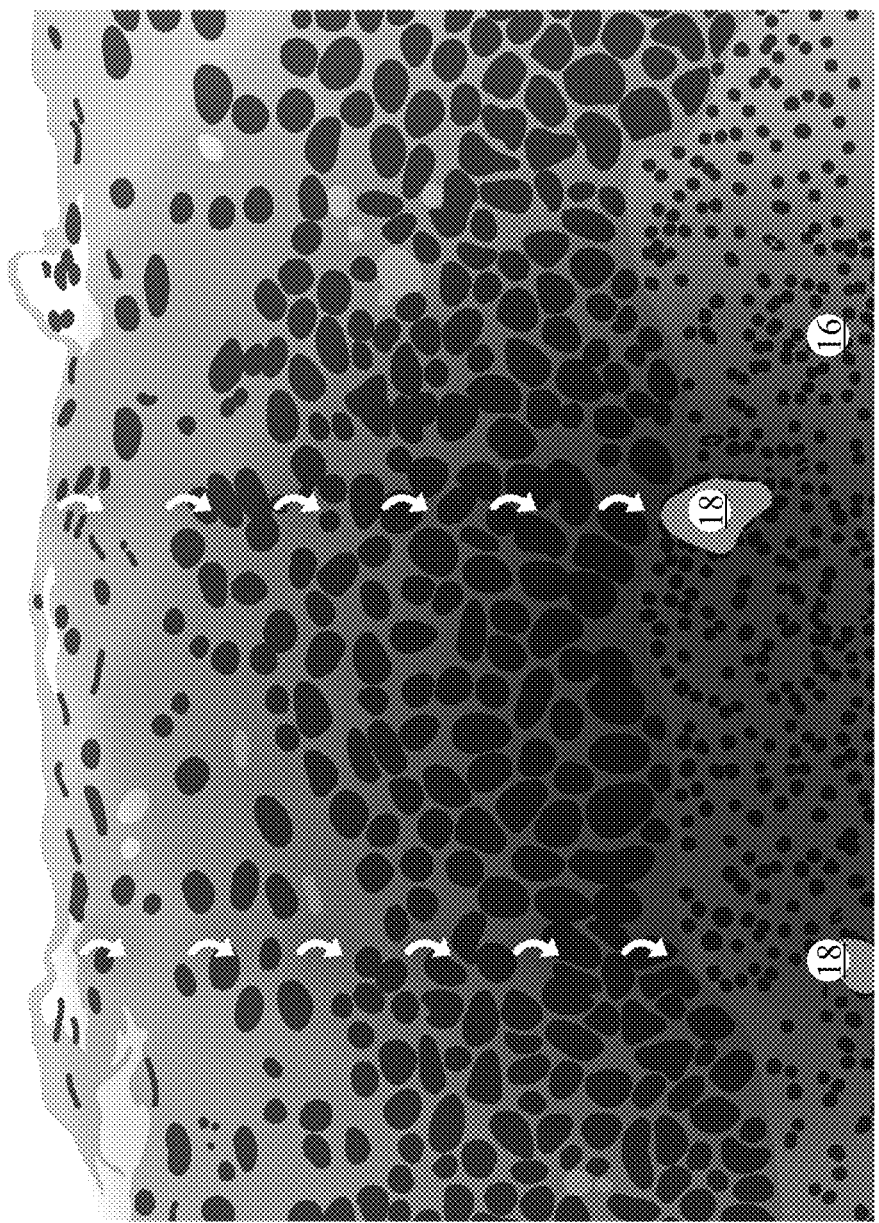
FIG. 13 shows a schematic micrograph of dysplastic squamous mucosa.

In other embodiments, application of an excess of the salvage nucleobase uracil together with 5-FU at a clinically-relevant dose (10 μM) prevented 5-FU toxicity in primary human epithelial cells of the gingiva (HEGP). FIG. 9 shows that uracil, but not adenine, is effective and non-toxic to primary gingival cells (HGEP) from 5-FU toxicity. Specifically, adenine and orotate at 2.5 mM each provides no protection against 5-FU toxicity (FIG. 9, Result W vs. Result X). The further addition of uracil at 1.25 mM provides significant protection (FIG. 9, Result Y), the further addition of uracil at 2.5 mM provides even more significant protection (FIG. 9, Result Z). Differences in gene expression of pyrimidine metabolic enzymes between the tissue types were detected that likely explain the differential sensitivity to nucleobase protection of 5-FU toxicity. GI columnar cells rely for growth predominantly on de novo pyrimidine synthesis from nutrients in the GI contents. Squamous cells of the oropharynx rely for growth predominantly on salvage of cell constituents of the overlying cells closer to the tissue surface.

Evidence for a clinical role for uracil protection from 5-FU toxicity already exists. Systemic uracil is a component of UFT (ftorafur plus uracil) that is in clinical use and UFT is well-tolerated and, in contrast to the administration of 5-FU alone, has a very low incidence of "hand-foot" syndrome (see, for example, Hoff, "The Tegafur-based Dihydropyrimidine Dehydrogenase Inhibitory Fluoropyrimidines, UFT/leucovorin (ORZEL) and S-1: A Review of their Clinical Development and Therapeutic Potential", *Invest. New Drugs*, Vol. 18, pp. 331-342, 2000). Topical uracil has been applied clinically and has prevented "hand-foot" syndrome from 5-FU treatment. It is important to note that the dose required in the present context is much lower than that often cited (100 mg/kg body weight). In some embodiments, topical uracil is applied to the tissue of the mouth to prevent oral stomatitis.

Correlative studies of mRNA expression in two colon cancer cell lines (Caco-2, HT-29) and primary human epithelial cells of the gingiva (HEGP) as well as clinical samples of normal esophageal and gastric tissue show that pyrimidine salvage pathway transcripts predominate in oral and esophageal cells of squamous histology whereas de novo pyrimidine synthesis predominates in gastric and colon tumor cells with columnar histology.

The directed application of the normal nucleobase uracil to oral mucosa (as well as skin) and of the normal nucleobase adenine to the GI tract, both sites of major 5-FU toxicity, to prevent 5-FU toxicity may represent a new paradigm in cancer supportive care. Likewise, the preservation to tissue under stress of the normal NDGP away from the zone of replication by the directed surface delivery of appropriate nutrients/treatments and the inhibition of the reversal of the NDGP through inhibition of mesenchymal neovascularization may also represent a new paradigm in arresting/reversing the epithelial oncogenic process.

The difference in nutrient utilization reported above also suggests a fundamental feature of epithelial oncogenesis. Cells of squamous histology in the GI tract, for growth, predominantly salvage cell components from the overlying cells as they move progressively away from the zone of replication and towards the surface. The columnar cells of the GI tract, for growth predominantly rely on de novo synthesis from nutrients derived from the contents within the GI tract. Columnar cells also migrate away from the zone of replication at the crypt base and towards the source of nutrients at the top of the crypt. The normal nutrient-driven growth polarity (NDGP) for both is away from the zone of replication. With dysplasia, the normal NDGP is inadequate to meet the tissue metabolic requirements. A new dominant NDGP with reversed polarity emerges that originates from neovasculature evoked from within underlying mesenchymal layer. This creates, for both squamous and columnar cells growth towards, rather than away from, the zone of replication. The result is a Darwinian competition for nutrients and survival at the zone of replication and, if sustained, oncogenesis.

Tissue cell-type differences in pyrimidine metabolism suggest a fundamental aspect of oncogenesis as well (see FIG. 10 through FIG. 13). Zones of cell turnover 10, zones of replication 12, myoepithelial layers 14, mesenchymal layers 16, and blood vessels 18 are labeled in FIG. 10 through FIG. 13. The normal NDGP for squamous cells in the GI tract results from progressive loss and reutilization of cell components as cells migrate towards the mucosal surface. A consequence is that squamous cells normally migrate progressively away from the zone of replication.

Likewise, for columnar cells, the normal NDGP also is away from the zone of replication at the base of the crypt. The cells migrate towards the top of the crypt and the nutrient source in the GI lumen. At the top of the crypt the cells are shed.

As clearly the first layer of epithelial cells for both squamous and columnar cell types must derive nutrition from the mesenchymal layer below, the normal response of tissue to nutrient stress is a transient reversal of NDGP, such as likely occurs in wound healing and in ontogeny. The oncogenic risk of reversed NDGP is a function of its persistence.

For both squamous and columnar cells, persistent nutrient stress causes a sustained reversal of nutrient polarity and thus a reversal in cell growth polarity. The persistent deficient nutrient availability could result from a decreased normal nutrient supply or increased demand exceeding the capacity. With sustained stress from deficient nutrient availability, both squamous and columnar cells elaborate HIF1-α (Levine et al., "Autophagy in the Pathogenesis of Disease", *Cell*, Vol. 132, pp. 27-42, 2008). HIF1-α is synthesized in response to anoxia or lack of glucose. The cellular release of HIF1-α results in a proliferation of new blood vessels in the underlying mesenchymal layer.

With dysplasia, the predominant nutrient supply comes from across the zone of replication from the underlying mesenchymal layer. The sustained reversal of the NGDP for both squamous and columnar cells results in a tissue in which the epithelial layer growth pattern is inverted. For columnar cells, crypt architecture is lost. The region of cell turnover is replaced by a tissue where all the epithelial cells grow towards the muscularis mucosae and intestinal subepithelial myofibroblasts. The consequence is that all the cells within the epithelial monolayer compete for nutrients from the underlying vasculature progressively as they increase in number. For cells of both squamous and glandular histology, the sustained reversal of the NDGP causes both the replication zone to expand above the epithelial/mesenchymal interface and the concomitant loss of the region of cell turnover. This Darwinian selection pressure, if sustained, leads to phenotypic and genotypic evolution of the epithelial cells at the epithelial/mesenchymal interface. This oncogenic process may progress to a breach by the epithelial cell of the basement membrane and EMT (epithelial mesenchymal transformation) in the competition for nutrients.

Support for this model of reversed NDGP in oncogenesis comes from explanations it provides for several currently puzzling clinical and research observations.

*H. Pylori* is a bacterial infection that involves the glycocalyx or superior aspect of gastric columnar cells. *H. Pylori* is not directly mutational to the underlying gastric cells. Yet *H. Pylori* infection can lead to cancer. However, *H. Pylori* uses glucose as a nutrient source and H. Pylori infection may be causing a local nutrient stress to the underlying glandular cells and could lead to reversal of NDGP.

The esophagus and the colon are vastly more likely than the small bowel to undergo epithelial cell oncogenesis. The present model would suggest that this could be due to the fact that vastly more nutrients are available and are absorbed by the columnar enterocytes of the small bowel than either the squamous cells of the esophagus or the columnar colonic epithelial cells (Roesly et al., "The Decreased Expression of Beclin-1 Correlates with Progression to Esophageal Adenocarcinoma: The Role of Deoxycholic Acid", *Am J. Physiol. Gastrointest. Liver Physiol.*, Vol. 302, pp. G864-G872, 2012).

Although both complete and incomplete intestinal metaplasia portend increased risk of cancer, complete intestinal metaplasia of the stomach (often due to *H. Pylori*) is less likely than incomplete metaplasia (columnar cells without absorptive enterocytes, i.e., goblet cells) of the esophagus to lead to epithelial cell cancer. The model of reversal of NDGP would suggest that oncogenic risk is enhanced for squamous mucosa that, instead of replicating normally every 21 days, is changed into a metaplastic glandular tissue that replicates much faster. The stomach with sufficient nutrients in the GI contents to lead to absorptive enterocytes, like the small bowel, would be less likely, despite the frequent presence of *H. Pylori*, to be associated with local nutrient deficiency than the incomplete metaplasia of the esophagus that depends on an uncertain nutrient source.

The molecular basis for the normal nutrient gradient is unknown. What is clear is that, for a tissue, cell turnover needs to be linked to nutrient availability. A tissue that is nutrient deprived cannot have uncontrolled cell turnover without compromising tissue integrity. The cell turnover that does occur needs to be limited in extent. The process cannot consume the epithelial cells at the epithelial/mesenchymal interface. Certain characteristics of autophagy may provide a control mechanism for epithelial tissue cell turnover. Autophagy occurs when an isolation membrane forms and then is transformed into a double membrane vesicle, autophagosome. The autophagosome delivers its contents to the lysosome for degradation. Autophagy is currently understood to be a response to the stress of nutrient deficiency at the level of the cell.

Autophagy may have also an apparently paradoxic function as a tissue protective system where autophagy determines the adequacy of nutrient availability to allow cell turnover. A role for autophagy in maintaining tissue structure has been shown in the necessity for autophagy in proper salivary gland degradation in *Drosophila*.

Beclin-1(atg-6) (coiled-coil, myosin like BCL-2 interacting protein) is an essential autophagy protein. Beclin-1(atg-6) double deletion in mice results in an abnormal ectodermal layer and early embryonic lethality. Beclin-1 includes a BH3 domain that interacts with Bcl-2/Bcl-X1 and inhibits Beclin-1 function. BCL-2 binding to Beclin-1 is inhibited by JNK1 phosphorylation of BCL-2. This modification is induced by starvation. An alternative mechanism of inhibition is phosphorylation of the BH3 domain on the Beclin-1 molecule by death-associated protein kinase (DAPK). This modification, in contrast to BCL-2 phosphorylation, because of the modification to the Beclin-1 molecule itself, creates a constitutively active Beclin-1. Thus, the DAPK activated Beclin-1 in contrast to JNK1 activated Beclin-1 can lead to cell death. As cells in intestinal glandular tissue move away from the zone of replication, the expression of DAPK increases as the cells approach the top of the crypts. The increased DAPK at the crypt tops also increases the probability of Beclin-1 phosphorylation and constitutive activation of autophagy.

Evidence of a role for extracellular factors in initiating autophagy exists. In contrast to the nutrient deficiency as a trigger for autophagy, administration of high glucose solution to cultured podocytes results in increased expression of Beclin-1 and autophagy (see, for example, Ma et al., "High Glucose Induces Autophagy in Podocytes", *Experimental Cell Research*, Vol. 319, pp. 779-789, 2013).

For GI glandular cells, the normal nutrient gradient is derived in significant part from the GI contents. The nutrients in the GI contents may thus initiate autophagy. The detachment process itself at the crypt top may be mediated by Ephrin ligand that can be sensitive to high glucose levels, in contrast to Eph receptor in the replication zone at the crypt base that can be sensitive to low glucose states.

Squamous cells have a much slower replication time than GI glandular cells. Our results suggest that squamous cells significantly salvage nutrients. As the cells migrate away from the zone of replication and the primordial nutrient source, they come under progressive nutrient stress. The cells may activate both JNK1 and DAPK autophagic pathways. The nutrient gradient develops as the nutrients released by the cells, progressively more remote from mesenchymal layer and the stimulus to cell replication that might otherwise consume the nutrients, increase.

The expression of Beclin-1, present throughout the tissue of both normal squamous and glandular cell GI histologies, decreases with progressive dysplasia. Beclin-1 expression may be a marker for the presence of normal NDGP.

In summary, the sustained reversal of normal NGDP has, as its cardinal feature, a nutrient source originating from the mesenchymal side of the zone of replication.

As has been described here with uracil and adenine to prevent 5-FU toxicity, in some embodiments, novel interventions involve the local delivery of an appropriate nutrient/therapeutic composition, likely including glucose, to dysplastic tissues. In some embodiments, the success of a specific intervention is determined by monitoring the restoration of normal Beclin-1 expression.

All above-mentioned references are hereby incorporated by reference herein.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

I claim:

1. A method for prevention of gastrointestinal toxicity in a plurality of gastrointestinal cells caused by administration of 5-fluorouracil to a cancer patient, the method comprising the steps of:
   a) administering the 5-fluorouracil to the cancer patient at a treatment dosage sufficient to cause a cancer cell toxicity of cancer cells of the cancer patient; and
   b) administering adenine to the cancer patient at a sustained dosage sufficient to prevent gastrointestinal toxicity in the plurality of gastrointestinal cells from the 5-fluorouracil administered in step a) but insufficient to give a systemic level of adenine to salvage the cancer cells from the cancer cell toxicity of the 5-fluorouracil administered in step a), wherein the sustained dosage provides the adenine at a concentration of at least 0.125 mM to the plurality of gastrointestinal cells of the cancer patient and wherein gastrointestinal toxicity is prevented.

2. The method of claim 1, wherein the adenine is orally administered to the cancer patient.

3. The method of claim 1, wherein the adenine is administered in an osmotically-controlled oral drug delivery device.

4. The method of claim 1, wherein the adenine is administered in cationic liposomes.

5. The method of claim 1 further comprising administering allopurinol to the cancer patient.

6. The method of claim 1, wherein the sustained dosage provides the adenine at a concentration of at least 0.62 mM to the plurality of gastrointestinal cells of the cancer patient.

7. The method of claim 1, wherein the sustained dosage provides the adenine at a concentration of at least 1.25 mM to the plurality of gastrointestinal cells of the cancer patient.

8. The method of claim 1, wherein the sustained dosage provides the adenine at a concentration in a range of 0.125 mM to 2.5 mM to the plurality of gastrointestinal cells of the cancer patient.

9. The method of claim 1, wherein step b) further comprises administering orotate to the cancer patient at a sustained dosage in combination with the adenine sufficient to prevent gastrointestinal toxicity in the plurality of gastrointestinal cells from the 5-fluorouracil administered in step a) but insufficient to give a systemic level of orotate to salvage the cancer cells from the cancer cell toxicity of the 5-fluorouracil administered in step a), wherein the sustained dosage provides the orotate at a concentration of at least 1.25 mM to the plurality of gastrointestinal cells of the cancer patient.

10. The method of claim 9 further comprising administering a proton pump inhibitor to the cancer patient.

11. The method of claim 1, wherein the treatment dosage exposes the plurality of gastrointestinal cells of the cancer patient to a concentration of the 5-fluorouracil of 0.01 mM.

12. The method of claim 1, wherein the sustained dosage is sustained for 120 hours.

13. The method of claim 1, wherein the plurality of gastrointestinal cells comprises substantially all gastrointestinal cells of the cancer patient such that the method prevents gastrointestinal toxicity in substantially all gastrointestinal cells of the cancer patient.

* * * * *